United States Patent [19]

Baltimore et al.

[11] Patent Number: 4,751,083
[45] Date of Patent: Jun. 14, 1988

[54] PRODUCTION OF NEUTRALIZING ANTIBODIES BY POLYPEPTIDE VP1 OF ENTEROVIRUSES AND BY OLIGOPEPTIDE FRAGMENTS OF POLYPEPTIDE VP1

[75] Inventors: David Baltimore; Marie B. Chow, both of Cambridge, Mass.

[73] Assignee: Massachusetts Institute of Technology, Cambridge, Mass.

[21] Appl. No.: 75,595

[22] Filed: Jul. 20, 1987

Related U.S. Application Data

[63] Continuation of Ser. No. 935,165, Nov. 25, 1986, abandoned, which is a continuation of Ser. No. 475,094, Mar. 14, 1983, abandoned, which is a continuation-in-part of Ser. No. 375,551, May 6, 1982, abandoned.

[51] Int. Cl.$^4$ ............................................. A61K 39/42
[52] U.S. Cl. .................................... 424/86; 436/543; 436/547; 435/68; 435/240.27; 530/324; 530/806; 530/809; 530/388; 514/12
[58] Field of Search ............... 424/85, 86; 260/112 R; 514/12; 530/324, 806, 809, 388

[56] References Cited

U.S. PATENT DOCUMENTS 4,544,500 10/1985 Bittle et al. ...................... 530/324

FOREIGN PATENT DOCUMENTS

| 81302080.7 | 5/1981 | European Pat. Off. . |
| 81107367.5 | 9/1981 | European Pat. Off. . |
| 82303040.8 | 6/1982 | European Pat. Off. . |
| PCT/US83/-00477 | 4/1983 | PCT Int'l Appl. . |
| PCT/GB83/-00254 | 10/1983 | PCT Int'l Appl. . |

OTHER PUBLICATIONS

Bachrach, H. L., Moore, D. M., McKercher, P. D. and Polatnichk, J., "Immune and Antibody Responses to an Isolated Capsid Protein of Foot-and-Mouth Disease Virus", *J. Immunol.* 115: No. 6, pp. 1636–1641 (1975).

Meloen, R. H., Rowlands, D. J. and Brown, F., "Comparison of the Antibodies Elicited by the Individual Structural Polypeptides of Foot-and-Mouth Disease and Polioviruses", *J. GenVirol.* 45:761–763 (1979).

Icenogle, J., Gilbert, S. F., Grieves, J., Anderegg, J. and Rueckert, R., "A Neutralizing Monoclonal Antibody Against Poliovirus and Its Reaction with Related Antigens", *Virology*, 115:211–215 (1981).

Blondel, B., Crainic, R. and Horodniceanu, F., "Le Polypeptide Structural VP1 du Poliovirus Type 1 Induit des Anticorps Neutralisants", *C. R. Acad. Sc. Paris*, t294 [Serie III-91 (19820)].

Knauert et al., "Monoclonal Antibody Specific for the D Antigenic Form of Poliovirus" in: *Abstracts of Ann. Mtg. Amer. Soc. Microbiology*, 81, 1981 (US), Abstract T126, p. 258.

Humphreys, D. D. et al., "Monoclonal Antibodies of 4 Different Specificities for Neutralization of Type I Polioviruses", *Biological Abstracts*, 74, No. 10, 1982.

Osterhaus et al., "Monoclonal Antibodies to Polioviruses: Production of Specific Monoclonal Antibodies to the Sabin Vaccine Strains", *Biological Abstracts*, 74, 1982.

*Primary Examiner*—Ronald W. Griffin
*Attorney, Agent, or Firm*—Hamilton, Brook, Smith and Reynolds

[57] ABSTRACT

The production of neutralizing antibodies for poliovirus, or other enteroviruses, are disclosed herein employing the capsid polypeptide VP1. Vaccines can be produced employing this polypeptide in place of killed or live attenuated virus, and the VP1 polypeptide can be employed in assays in place of whole virions. VP1 polypeptide can be produced by isolating it from live virion or can be produced by cloning cDNA sequences coding for this protein in recombinant cDNA vectors.

14 Claims, No Drawings ma # PRODUCTION OF NEUTRALIZING ANTIBODIES BY POLYPEPTIDE VP1 OF ENTEROVIRUSES AND BY OLIGOPEPTIDE FRAGMENTS OF POLYPEPTIDE VP1

GOVERNMENT SUPPORT

The work described herein was supported by one or more grants from The National Institutes of Health.

RELATED APPLICATIONS

This is a continuation of co-pending application Ser. No. 935,165, filed Nov. 25, 1986, which is a continuation of Ser. No. 475,094, filed on Mar. 14, 1983, which is a continuation-in-part of Ser. No. 375,551, filed May 6, 1982, all now abanonded.

TECHNICAL FIELD

This invention is in the field of virology.

BACKGROUND ART

Poliovirus, one of the human picornaviruses of the enterovirus subgroup, has been extensively studied because it is the causative agent for serious human disease. Because of these studies, it is now known that the virion of poliovirus consists of a small icosahedron, 25–30 nm in diameter, composed of four polypeptides, which are designated VP1, VP2, VP3 and VP4. A single strand of infectious positive-stranded RNA of molecular weight $2.7 \times 10^6$ daltons is enclosed within this protein coat. This size is equivalent to approximately 7500 bases, which can code for about 2500 amino acids.

The first significant breakthrough in research directed to limiting the spread of epidemics of poliovirus was attained by the development of a killed virus vaccine for poliovirus by Jonas Salk in 1953. See Salk, J. E. with the collaboration of Bennett, B. L., Lewis, L. J., Ward, E. N., and Youngner, J. S., "Studies in Human Subjects on Active Immunization Against Poliomyelitis. I. A Preliminary Report of Experiments in Progess.", *J. Am. Med. Assoc.* 151 1081–1098 (1953). Preparation of the Salk killed virus vaccine was achieved by producing large amounts of virus in cell culture and subsequently treating the infected tissue culture fluid with formalin to inactivate the virus particles.

More recently, live attenuated polio vaccines have been developed. See Koprowski, H., Jervis, G. A. and Norton, T. W., "Immune Response in Human Volunteers Upon Oral Administration of A Rodent Adapted Strain of Poliomyelitis Virus", *Am. J. Hyg.* 55 108–126 (1952); and Sabin, A., "Properties of Attenuated Poliovirus and Their Behavior in Human Beings", *Spec. Publ. N. Y. Acad. Sci.* 5, 113–127 (1957). Live attenuated polio vaccine proved to be equal to or more effective than killed polio virus vaccine in reducing the incidence of poliomyelitis and possessed substantial practical and theoretical advantages. Such vaccines were simple to administer and entered through the normal routes, and were found to induce higher levels of circulating antibody as well as the production of IgA antibody from local exocrine cells.

Despite the marked success achieved by prior polio vaccines, there remains even today a strong desire to develop new vaccines which would be easier to manufacture than the Salk vaccine and eliminate or substantially diminish the possibility of attenuated viruses regaining virulence and therefore becoming capable of infecting recipients.

In particular, there has been much research devoted towards determining whether subviral poliovirus components, particularly any of the capsid polypeptides VP1, VP2, VP3 or VP4, might be capable themselves of producing neutralizing antibodies upon injection into a host. If such subviral components could produce neutralizing antibodies, there would be great advantages in forming vaccines from such subviral components since there would be no possibility that such components could be infectious and since such components could most likely be produced in commercial quantities by cloning the gene sequence of such components in a recombinant cDNA vector.

Support for the belief that individual capsid polypeptides of poliovirus might be capable of generating neutralizing antibodies was initially based upon research with isolated capsid proteins of foot-and-mouth disease virus. In this work, one of the capsid proteins of foot and mouth disease virus, termed VP3 (sometimes VP$_t$ or even VP$_1$), was isolated and injected into swine and guinea pigs. It was found that the foot-and-mouth virus polypeptide VP3 was capable of initiating neutralizing antibody production in both. On the other hand, neutralizing antibodies were not produced in response to immunization with VP1 or VP2 polypeptides isolated from the foot and mouth disease virus capsid. See Bachrach, H. L., Moore, D. M., McKercher, P. D. and Polatnick, J., "Immune and Antibody Responses to an Isolated Capsid Protein of Foot-and-Mouth Disease Virus", *J. Immunol.* 115, No. 6, pp 1636–41 (1975). It was also demonstrated that mengovirus, another member of the aphthovirus subgroup, also produced neutralizing antibody in animals, Lund, G. A., Ziola, B. R., Salmi, A. and Scroba, D. G., "Structure of the Mengo Virion. V. Distribution of the Capsid Polypeptides With Respect to the Surface of the Virus Particle," *Virology* 78, 35–44 (1977).

Despite this work with foot-and-mouth virus and mengovirus, attempts to produce neutralizing antibodies from capsid polypeptides of the poliovirus met with no success or were inconclusive. For example, Meloen et al. compared the individual capsid polypeptides of foot-and-mouth and polio viruses and found that none of the individual polypeptides from poliovirus produced antisera which neutralized the virus. See Meloen, R. H., Rowlands, D. J. and Brown, F., "Comparison of the Antibodies Elicited by the Individual Structural Polypeptides of Foot-and-Mouth Disease and Polioviruses", *J. Gen Virol.* 45, 761–3 (1979).

Icenogle et al. prepared a neutralizing monoclonal antibody against Type 1 poliovirus and attempted to determine the affinity of this monoclonal antibody against various subviral particles. The monoclonal antibody had a much higher affinity for the 14S subunit than for similar subunits lacking the VP1 polypeptide, leading the authors to conclude that the VP1 polypeptide had an important role in the production of neutralizing antibodies. However, the monoclonal antibody had an almost insignificant affinity for the individual polypeptides. See FIG. 2, Icenogle, J., Gilbert, S. F., Grieves, J., Anderegg, J. and Rueckert, R., "A Neutralizing Monoclonal Antibody Against Poliovirus and Its Reaction With Related Antigens", *Virology* 115, 211–15 (1981). Similar reasoning had earlier led Breindl to conclude that the VP4 polypeptide of poliovirus contained the reactive antigenic determinants. See Breindl, M., "VP4, The D-Reactive Part of Poliovirus," *Virology* 46; 962–64 (1971). VP4, however, is not present on the surface of the poliovirus capsid and is not presently believed to be capable of producing neutralizing antibodies today.

The most recent report in the literature concerning efforts to produce neutralizing antibodies with poliovirus capsid polypeptides presents the results of Blondel et al. at the French Academy of Science. See Blondel, B., Crainic, R. and Horodniceanu, F., "Le Polypeptide Structural VP1 du Poliovirus Type 1 Induit Des Anticorps Neutralisants", *C. R. Acad. Sc. Paris, t*294 (Serie III-91(1982). In this report, the researchers state that the poliovirus polypeptide VP1 produced neutralizing antibodies in one of two rabbits they immunized. Data were not reported, however, to rule out the possibility that the VP1 generated antisera recognized antigenic determinants present on the VP2 or VP3 proteins.

DISCLOSURE OF THE INVENTION

This invention relates to the surprising discovery that one of the poliovirus capsid polypeptides, VP1, is capable of producing neutralizing antibodies for poliovirus. Further, it has been discovered that certain oligopeptide fragments of the poliovirus capsid polypeptide, VP1, are themselves capable of producing neutralizing antibodies for poliovirus.

Based upon this discovery, it is now clear that the poliovirus capsid polypeptide VP1 or oligopeptide fragments thereof can be employed in place of whole poliovirus particles in the production of antibodies to poliovirus.

In addition, vaccines for poliovirus can be based upon the VP1 polypeptide or oligopeptide fragments thereof rather than the whole virion. This will facilitate the production of vaccines to poliovirus and will eliminate any possibility of the vaccine containing a virion which could revert to virulence thereby becoming capable of infecting the recipient with polio.

The VP1 polypeptide can be isolated from the poliovirus virions employing methods which dissociate the virions into individual polypeptides after which such polypeptides can be separated. One specific method is carried out by boiling poliovirus virions for limited periods of time to separate the various polypeptides and subsequently separating individual polypeptides on a polyacrylamide gel.

A more preferred method for obtaining the VP1 polypeptide, however, is by employing standard recombinant cDNA techniques. In such techniques, gene sequences coding for the VP1 polypeptide are inserted into a recombinant cDNA vector, such as a bacterial plasmid, followed by the isolation of a bacterial strain carrying the chimeric plasmid. The bacterial strain can then be cultured under conditions whereby it will express VP1 protein. In addition to the usual advantages gained by employing recombinant cDNA techniques to produce proteins, such techniques produce a VP1 polypeptide which has a native structure in this particular case contrasted to the denatured structure, obtain by many of the techniques for isolating VP1 polypeptide from native poliovirus virions.

It is also believed that the VP1 polypeptide of other viruses or oligopeptide fragments of these VP1 polypeptides, within the enterovirus subgroups are capable of producing neutralizing antibodies to their respective whole virus particles.

The oligopeptide fragments of the VP1 polypeptide may be chemically synthesized, or alternatively, the fragments may be obtained by enzymatically cleaving the VP1 polypeptides. In addition, the oligopeptide fragments may be obtained by employing recombinant DNA techniques. The techniques are essentially the same as those described for obtaining the entire VP1 polypeptide. The cloned gene sequence is that which codes for the desired oligopeptide fragment.

BEST MODE FOR CARRYING OUT THE INVENTION

As used herein, the term "VP1 polypeptide" means the whole protein sequence present in the VP1 polypeptide found in native enterovirus particles or a significant portion thereof. In other words, the term is employed for polypeptides containing essentially all of the amino acids present in the native VP1 polypeptide but possibly omitting a few such sequences which do not interfere with the ability of the polypeptide to produce neutralizing antibodies. As those skilled in the art will understand, it sometimes happens that the VP1 polypeptide produced by recombinant cDNA techniques may lack a few amino acids present in the native VP1 polypeptide, but these amino acids are not essential for the production of neutralizing antibodies to poliovirus by the VP1 polypeptide produced in such recombinant cDNA procedures. The term "oligopeptide fragment" of poliovirus capsid polypeptide VP1 means any polypeptide which has an amino acid sequence that corresponds substantially with a particular portion of the amino acid sequence of the VP1 polypeptide. The term is meant to include oligopeptides which have been modified by the insertion, deletion, substitution of amino acids or by the modification of constituent amino acids.

Type I poliovirus was employed in the work described herein. Such virus can be obtained by growing epithelioid cells in suspension culture and infecting the culture with poliovirus, Type I. The infected cells can then be lysed with detergent to release virus particles which can be purified by centrifugation.

The oligopeptide fragments of poliovirus capsid polypeptide VP1 having designated amino acid sequences were chemically synthesized by Richard Lerner. See, Green et al. *Cell* 28:477–487 (1982). The method of synthesis employed was the solid state method originally developed by Merrifield et al.

It is also believed that VP1 polypeptide from Type II and Type III poliovirus can be employed to produce neutralizing antibodies to Type II poliovirus and Type III poliovirus, respectively. Similarly, it is believed that VP1 polypeptide or oligopeptide fragments of the VP1 polypeptide, of other viral members of the enterovirus subgroup, such as coxsackie viruses and echo viruses, can be employed to produce neutralizing antibodies to their respective whole virus particles.

Each of the isolated capsid polypeptides, VP1, VP2 and VP3 have been tested to determine whether they produced antibodies which are specific to VP1, VP2 and VP3 respectively. In each case, antibodies having such specificity were produced. However, it was found that only VP1 was capable of producing neutralizing antibodies upon injection intraperitoneally and intradermally into rats.

For vaccine production it may be desirable, in some cases, to mix the VP1 polypeptide with one or both of the VP2 and/or VP3 polypeptide, or other poliovirus subunits. In vaccines produced from oligopeptide fragments of the VP1 polypeptide, it may be desirable to include a mixture of various oligopeptide fragments.

Of course, vaccines based upon isolated enterovirus VP1 polypeptide or polypeptide fragments of the VP1 polypeptide will normally also contain adjuvants, stabilizers, etc. Those skilled in the art will know, or be able to ascertain using no more than routine experimentation, such additional vaccine components which are desirable in each particular case.

Antibodies to poliovirus are produced by employing the VP1 polypeptide in standard antibody production techniques. Thus, for producing polyclonal antibodies, the VP1 polypeptide is employed to immunize a host, such as a rabbit or rat, and antibodies to the VP1 polypeptide are subsequently collected from serum obtained from the host. To produce polyclonal antibodies against poliovirus using oligopeptide fragments of VP1, the polypeptide fragments may be administered to the host in a form chemically coupled to a carrier protein such as Keyhole Limpet Hemacyanin, or they may be administered in uncoupled form.

Alternatively, monoclonal antibodies can be produced employing cells which produce antibodies to the VP1 polypeptide or to an oligopeptide fragment thereof in typical fusion techniques for forming hybridoma cells. Basically, these techniques involve the fusing of the antibody producing cell with a cell having immortality, such as a myeloma cell, to provide a fused cell hybrid which has immortality and is capable of producing the desired antibody, in this case antibody to the VP1 polypeptide or to a oligopeptide fragment thereof. The hybrid cells are then cultured under conditions conducive to the production of antibody which is subsequently collected from the cell culture medium. Such techniques for producing monoclonal antibodies have been well described in the literature. See, for example, U.S. Pat. No. 4,196,265 issued to Hillary Koprowski et al., the teachings of which are hereby incorporated by reference.

In the experimental work described below, it will be noted that Lewis rats were immunized with the VP1 polypeptide or with oligopeptide fragments of the VP1 polypeptide and shown to produce antibodies to this polypeptide and to certain oligopeptide fragments thereof. Thus, the cells from the spleen of such immunized rats would be ideal candidates for fusing with myeloma cells to produce hybridoma cell lines capable of yielding monoclonal antibodies to the VP1 polypeptide.

Another significant use for the VP1 polypeptide of poliovirus and the oligopeptide fragments of this polypeptide is in assays to detect the presence of whole poliovirus particles. Such assays include immunoassays, such as those radioimmunoassays employing labelled antibodies or viral antigens. In such assays, VP1 polypeptide or an oligopeptide fragment thereof could be substituted for whole poliovirus particles, or antibodies to VP1 polypeptide could be substituted for antibodies to the whole poliovirus variant. Similarly, VP1 polypeptide or oligopeptide fragments can be substituted for poliovirus particles, or antibodies to VP1 polypeptide or oligopeptide fragments of the VP1 polypeptide can be substituted for antibodies to poliovirus particles, in enzymes employing other labels, such as those employing enzyme labels.

VP1 polypeptide can be produced by cloning cDNA sequences coding for this protein. In such cloning, fundamental gene splicing techniques, which have been described in the scientific and patent literature are employed. For example, U.S. Pat. No. 4,227,224, issued to Stanley N. Cohen and Herbert W. Boyer on Dec. 2, 1980, describes many of these techniques. Similarly, U.S. patent application Ser. No. 320,525, filed Nov. 12, 1981 under the names of David Baltimore and Vincent R. Racaniello, describes specific techniques for producing cDNA for viral RNA sequences. Because of this, the teachings of both of the aforementioned documents are hereby incorporated by reference.

A specific technique employed to construct a plasmid which expresses poliovirus polypeptide VP1 will now be described. Initially, it was recognized that there were certain problems to overcome. For example, since VP1 is generated by protease cleavage of polyprotein, in vivo, the gene does not provide its own AUG, to initiate synthesis of the protein, or termination codon, to terminate synthesis of the protein. Additionally, a promoter, ribosome binding site, and transcription termination site needed to be provided.

The vector used was pCQV2, which was in the pBR322 background. Lambda genes were inserted into this vector. One gene employed, the $CI_{857}$, is a thermo-sensitive gene. CI protein controls transcription of $P_r$ promoter; when working, the CI protein shuts off transcription from the $P_r$ promoter. The protein coded for by the $CI_{857}$ gene is active at a temperature range of 30°–32° C. but inactive at a temperature range of 38°–42° C.

The rightward promoter of lambda, $P_r$, was also employed. This vector provides a ribosome binding site and AUG initiator codon placed after the $P_r$ promoter.

$pBR_{322}$ plasmid provided the transcription and translation termination sites.

Specifically, the Bam-Hinc II fragment of sub-clone pVR104 (See Ser. No. 320,525) was inserted in pBR322 from the Bam HI site to the Ava I site, and the plasmid was transformed into EcoRI RRI.

Selection of cells for $tet^s$, $amp^r$ was then made for cells containing polio sequences for VP1 and part of the 3B genes.

Since the polio fragment, $pBR_{322}$ and pCQV2 have several Hae II restriction endonuclease sites, partial cleavage with Hae II was done so that on average one cleavage per plasmid molecule resulted. The Hae II ends were trimmed with cDNA polymerase (Klenow fragment) and cut with EcoRI. The correct EcoRI-Hae II polio fragment was isolated on agarose gel.

pCQV2 was cut with Bam HI and filled in with cDNA polymerase, then cut with EcoRI, and the fragment containing the $CI_{357}$ gene and $P_r$ promoter was isolated. This fragment was ligated with the EcoRI-Hae II polio fragment and transformed into RRI. Suitable clones were then selected.

The clones selected, upon induction at higher temperatures, made a protein having a molecular weight of 55,000 daltons. This protein was processed down to 35,000 daltons by the clone, which is the size of the VP1 polypeptide. The processing generated the correct sequence of VP1 by analysis of partial protease products. This processing was surprising in view of the fact that such cleavages have been previously believed to have been performed by viral proteases which were thought not to be coded for by the cDNA sequence inserted into this clone. The 35,000 dalton protein was instable and degraded.

Although bacterial plasmids were actually employed in producing the VP1 polypeptide by recombinant cDNA methodology, other recombinant cDNA vectors can be employed. Examples of other recombinant cDNA vectors include phages, animal viruses and yeast vectors. Hosts which allow the recombinant cDNA vectors to multiply are chosen, of course.

This invention is now further and more specifically illustrated by the following Examples.

EXAMPLE

Preparation of Poliovirus

Poliovirus was obtained using standard procedures (Flanegan et al., 1977, *PNAS* 74:961). HeLa cells were grown in suspension culture to a density of $4 \times 10^5$ cells per ml, centrifuged, and infected with a stock of poliovirus, type 1, at a multiplicity of infection (MOI) of 10. Infection was allowed to proceed for six hours at 37°, at which time the cells were centrifuged. Virus was released from the cells with detergent and purified from the lysate by cesium chloride equilibrum centrifugation.

Isolation of Poliovirus Capsid Proteins

The capsid proteins, VP1, VP2 and VP3, were isolated by SDS-polyacrylamide gel electrophoresis by the method of Laemmli. See Laemmli, U. K., "Cleavage of Structural Proteins During the Assembly of the Head of Bacteriaphage T$_4$", *Nature* (London), 227, 680–85. The virions were disrupted by boiling for 10 minutes in 1% SDS-5 mM EDTA just prior to electrophoresis on a preparative 13% SDS-polyacrylamide gel. The separated proteins were visualized as clearing zones in the gel by precipitating the free SDS in the acrylamide gel with 2.5 M KCl. The protein bands were cut out and electroeluted overnight, then dialyzed against 10 mM Tris-HCl (pH 7.5)-1 mM EDTA (TE 7.5). The concentration of the eluted proteins was estimated on Commasie stained SDS-polyacrylamide gels by their staining intensity relative to the staining intensity of known concentrations of protein standards.

Preparation of Oligopeptide Fragments of Poliovirus Capsid Protein

Chemically synthesized oligopeptide fragments of the poliovirus capsid polypeptide VP1 having prescribed amino acid sequences were obtained from Richard Lerner at Scripps Clinic and Research Foundation, La Jolla, Calif. The oligopeptides were synthesized by the solid state method of Merrifield et al.

Immunizations

Polypeptide VP1

Male Lewis rats, eight weeks old were injected intraperitoneally and intradermally with emulsions containing 100 μg of the isolated proteins. To equalize any variability due to the response of the individual rats, a total of three rats were injected per protein sample. The emulsions were made by mixing equal volumes of the protein solution and complete Freunds adjuvant. After three weeks, the initial injection was followed by three booster injections two weeks apart. Each booster contained 100 μg of protein in 50% emulsion with incomplete Freunds adjuvant. Animals were bled from the ocular sinus 8–10 days after each boost. The serum was isolated and heated to 65° C. for 30 minutes before storage at −20° C. Sera were checked for the presence of antibodies against the injected antigen using Ouchterlony double diffusion plates.

Oligopeptide Fragments of Polypeptide VP1

Oligopeptide fragments of the VP1 polypeptide were administered either coupled to a carrier protein such as Keyhole Limpet Hemacyanin or uncoupled. To effect coupling, conventional coupling reagents such as glutaraldehyde and M-maleimide-benzoyl-N-hydroxy-succinimide ester were employed. Each rat was injected intraperitoneally, intradermally or subcutaneously according to the schedule set forth below with emulsions containing 100 μg of the oligopeptide fragments. A total of three rats were injected per protein sample. The emulsions were made by mixing equal volumes of the protein solution and complete or incomplete Freunds adjuvant The rats were given three priming injections two weeks apart. The initial injection was in complete Freunds adjuvant; the second and third injections were in incomplete Freunds adjuvant. The priming injections were followed by two boosting injections; both injections were in incomplete Freunds adjuvant and given four to six weeks apart. Animals were bled from the ocular sinus twelve days after the last boosting injection. Serum was isolated and treated as described above.

Neutralizing Titers

The titers of neutralizing antibody present in the serum were measured by two methods.

Half neutralization values were determined as follows. Two-fold serial dilutions of serum in PBS (phosphate-buffered-saline) were incubated with 200 PFU of poliovirus in a final volume of 200 μl for two hours at 25° C., then overnight at 4° C. The entire sample was placed undiluted onto HeLa cell monolayers in a standard plaque assay protocol. The neutralizing titer was defined as the serum dilution required to reduce the number of plaques by 50%.

Virus survival curves were also produced in order to quantitate the amount of virus killed by a given amount of serum. $10^7$ PFU of poliovirus was incubated with different dilutions of the rat sera in a final volume of 10 μl. Incubations were at 25° C. for two hours, then overnight at 4° C. The number of surviving infectious particles was measured by a polio plaque assay.

Plaque Assays

The virus titers were determined using cloned HeLa cell line S-3 which is carried in suspension but which will also grow on plates. HeLa cells were plated at $2 \times 10^6$ cells/60 mm plate in Dulbecco's modified medium containing 5% fetal calf serum (DME-5% FCS). After three hours at 37° C., the medium along with any floating cells was aspirated off and 200 μl of the virus antibody sample in PBS was placed on the monolayer. The plates were incubated for 30 minutes at 37° C. The plates were then overlayed with 5 ml of 1% agarose-DME-5% FCS and incubated at 37° C for thirty hours (Poliovirus, Type I, Mahoney strain) or for 54–72 hours (Poliovirus, Type II, Lansing strain). All plaque assays were done in duplicate. Plaques were visualized by staining with crystal violet.

$^{35}$S-Methionine Labeled Virions

HeLa cells in methionine minus medium were infected with Type I poliovirus (Mahoney) at MOI=10. Cells were labeled with $^{35}$S-methionine (1mCi/ml) at 3.5 hours post infection and harvested at 6 hours post infection. Cells were lysed in 1% NP-40-10 mM Tris, pH 7.5-10 mM NaCl-1.5 mM $MgCl_2$ and nuclei were spun out. The virus was pelleted in a 50Ti centrifuge rotor for one hour at 45,000 RPM. The virus pellet was resuspended in 10 mM Tris-HCl (pH 7.5)-1 mM EDTA-0.1 M-NaCl-0.5% SDS (TNE+0.5% SDS) and banded in cesium chloride. The virus band was isolated, dialyzed against TNE and stored at −20° C.

Radio-Labeling of Oligopeptide Fragments

Radiolabeled oligopeptide fragments were generated using $^{125}I$ and Chloramine-T by conventional methods.

Immune Precipitations

Immune precipitations were carried out in 10 mM Tris, pH 7.5, 0.15 M NaCl, 1% deoxycholic acid, 1% Triton X-100, 0.1% SDS (Ripa) in the presence of 0.5 mg/ml ovalbumin. In some cases, just prior to incubation with the antisera, samples were denatured by boiling 10 minutes in 1% SDS-5 mM EDTA and then spun 5 minutes in an eppendorf centrifuge. $^{35}S$-methionine labeled or $^{125}I$ labeled samples were incubated with a given amount of antisera for two hours at room temperature and then incubated with 10 fold serum volumes of a 10% solution containing formalin-fixed Staph A (New England Enzyme Center, IgGsorb) for 30 mintues at 0° C. The Staph A was spun 30 seconds in an eppendorf centrifuge and the Staph A pellet was washed three times with 1 ml of Ripa - 0.5M NaCl, then 1 ml of Ripa-0.15 M NaCl. $^{125}I$-labeled immune precipitated samples were counted in a gamma counter. $^{35}S$-Methionine immune precipitated samples were electrophoresed in an 11% SDS-polyacrylamide gel according to the technique of Laemmli. Staph A containing samples were boiled in the SDS sample buffer for 10 minutes; the Staph A was spun out and the supernatants were loaded onto the gel. The gels were fixed in 10% acetic acid-10% methanol, dried, and autoradiographed (Kodak, XAR film) at −70° C.

Results

Polypeptide VP1

All serum samples collected after each boost formed precipitin lines with the injected antigen when tested in ouchterlony double diffusion plates. To test the specificity and selectivity of these antisera, $^{35}S$-Methionine labeled poliovirus (Mahoney, Type I) was immune precipitated with these sera in Staph A. The precipitated samples were displayed on an 11% polyacrylamide gel and autoradiographed. Since the antisera had been raised against proteins isolated after boiling in 1% SDS, the virions were boiled in 1% SDS just prior to being incubated with the antisera. Antisera raised against VP1 precipitated specifically VP1 released from dissociated virions. Similarly, antisera raised against VP2 or VP3 precipitated only VP2 or VP3, respectively. None of the pre-immune sera from any of the rats precipitated virion proteins. In every gel, several sample lanes contained standards using the $^{35}S$-Methionine labeled virions unprecipitated at known protein concentrations. By comparing the intensity of the immunoprecipitated band with that of the virion standards, a value could be estimated for the number of antigen molecules precipitated by a known volume of serum. Thus, 2 μl of almost all of the rat sera tested after the second boost precipitated an amount of capsid protein equivalent to that found in $10^{10}$ particles; assuming there are 60 molecules in each capsid protein found in a virion particle, then 2 μl of the rat sera would precipitate approximately $1\times10^{12}$ molecules of antigen.

All of the antisera precipitated intact virions although with varying efficiencies. By comparing the intensities against virion standards, 2 μl of VP1 or VP2 antisera could precipitate approximately $10^9$ virion particles; 2 μl of VP3 antisera could precipitate approximately $10^8$ virions.

Since the antisera recognized antigenic determinants on the intact native virion particles, sera were tested for neutralizing activity. The half neutralization titers observed are presented in Table I.

TABLE I

NEUTRALIZING SERUM PRODUCTION IN RATS BY ISOLATED POLIOVIRUS, TYPE 1 PROTEINS

| Injected 4X c 100 ug of | Serum Dilution for 50% neutralization of 200 PFU: Preimmune | Immunized 4X | |
|---|---|---|---|
| VP1 | —(a) | 1/30–1/200 | (8/8+) |
| VP2 | — | — | (3/3−) |
| VP3 | — | — | (3/3−) |
| Virions (3/3+) | — | $1/10^{4}$(b) | |

(a) No detectable neutralization
(b) Titers given were from sera collected after 1st boost Only sera from rats which had been injected with VP1 showed any neutralizing titers. The VP2 and VP3 antisera showed no neutralizing activity even after the third boost. In constrast, after each boost with VP1, the neutralizing titers increased such that, after the third boost with VP1, the neutralizing titer had increased ten-fold over the neutralizing titer from the sera obtained after the first boost.

Although the VP1, VP2 and VP3 specific antisera from Type I poliovirus recognized VP1, VP2 and VP3 from poliovirus Type 2 virions, respectively, none of rat antisera showed any neutralizing activity against poliovirus, Type II.

The effect of the sera on high titers of virus is shown in Table II.

TABLE II

EFFECT OF RAT SERA ON $5\times10^7$ PFU OF POLIVIRUS, TYPE 1

| Antigen | Titer Reduction by Undiluted Serum |
|---|---|
| None | 0 |
| VP1 | 1/10–1/50 |
| VP2 | 0 |
| VP3 | 0 |
| Virions $10^{-3}$ | 1/100 (at dilution) |

No significant decrease in titers was seen when $5\times10^7$ PFU of poliovirus was incubated with undiluted pre-immune sera, anti-VP2 or anti-VP3 sera. In contrast, virus titers decreased approximately 1.5 $\log_{10}$ when anti-VP1 sera was incubated with the virus. Thus, rats injected with only VP1 produced sera which is capable of neutralizing poliovirus.

Since the neutralizing antisera generated by VP1-injected rats produced low titers, the neutralizing titers of sera from rats injected with whole virions was measured to see whether the titers were comparable. As is evident, the titers of sera obtained from virion-injected rats after the first boost is several $\log_{10}$ greater than the serum titers obtained from VP1-injected rats after the third boost (Tables I and II).

Consistent with the high neutralizing titers observed, the antisera quantitatively precipitated native virions. Thus, after the first boost, 2 μl of sera could immune precipitate approximately 10^10 virion particles. To see whether the antivirion sera recognized any of the individual virion proteins, SDS treated virions were immune precipitated with the sera. None of the rat serum recognized any of the denatured proteins.

Oligopeptide fragments of Polypeptide VP1

The oligopeptide fragments of polypeptide VP1, having the following amino acid sequences, were found to induce a neutralizing response to poliovirus SER—ILE—PHE—TYR—THR—TYR—GLY—THR—ALA—
PRO—ALA—ARG—ILE—SER—VAL—PRO—TYR—VAL—
GLY—ILE.

VAL—VAL—ASN—ASP—HIS—ASN—PRO—THR—LYS—
VAL—THR—SER—LYS—ILE—ARG—VAL—TYR—LEU—
LYS—PRO—LYS.

These oligopeptide fragments appear to represent certain regions of the polypeptide VP1 which are important in eliciting the production of antibodies. As would be recognized by one skilled in the art, additional oligopeptide fragments from these significant regions of the polypeptide VP1 which may exhibit the ability to induce the neutralizing response.

For example, by moving the region of interest of Polypeptide VP1, as it is represented by the above oligopeptide a few amino acids in either the C or N terminus direction, an oligopeptide fragment which induces a stronger response may be obtained.

Further, the oligopeptides may be modified in various ways to bring about a stronger response. For instance, amino acids may be deleted from the oligopeptide or amino acids or amino acid analogs may be inserted or added to the sequence. In addition, constituent amino acids may be chemically modified. Any of the procedures may lead to the discovery of an oligopeptide fragment which is a more potent inducer of the neutralization response against poliovirus.

Industrial Applicability

The invention described herein is useful in the production of vaccine and neutralizing antibodies to poliovirus or other enteroviruses.

Equivalents

Those skilled in the art will recognize, or be able to ascertain, using no more than routine experimentation, many equivalents to the specific embodiments of the invention described herein. Such equivalents are intended to be emcompassed by the following claims.

We claim:

1. In the production of neutralizing antibodies to poliovirus by immunizing antibody-producing cells with polioviirus antigen in vivo or in vitro and collecting the antibodies produced by the immunized cells, the improvement of employing isolated poliovirus capsid polypeptide VP1 as the antigen.

2. A method of claim 1, wherein the neutralizing antibodies react specifically with poliovirus capsid polypeptide VP1.

3. In the production of neutralizing antibodies to poliovirus by immunizing antibody-producing cells with poliovirus antigen in vivo or in vitro and collecting the antibodies produced by the immunized cells, the improvement of employing an oligopeptide fragment of poliovirus capsid polypeptide VP1 as the antigen which causes production of neutralizing antibodies to poliovirus.

4. An improvement according to claim 3 wherein the oligopeptide fragment is chemically synthesized.

5. An improvement according to claim 8 wherein the oligopeptide fragment has the following amino acid sequence:

SER—ILE—PHE—TYR—THR—TYR—GLY—THR—ALA—
PRO—ALA—ARG—ILE—SER—VAL—PRO—TYR—VAL—
GLY—ILE.

6. An improvement according to claim 3 wherein the oligopeptide fragment has the following amino acid sequence:

VAL—VAL—ASN—ASP—HIS—ASN—PRO—THR—LYS—
VAL—THR—SER—LYS—ILE—ARG—VAL—TYR—LEU—
LYS—PRO—LYS.

7. A method of claim 3, wherein the neutralizing antibodies react specifically with poliovirus capsid polypeptide VP1.

8. Poliovirus-neutralizing anitbody to isolated poliovirus VP1 polypeptide.

9. Poliovirus-neutralizing antibody to an oligopeptide fragment of poliovirus VP1 polypeptide.

10. An improvement according to claim 9 wherein the oligopeptide fragment is chemically synthesized.

11. An improvement according to claim 9 wherein the oligopeptide fragment has the following amino acid sequence:

SER—ILE—PHE—TYR—THR—TYR—GLY—THR—ALA—
PRO—ALA—ARG—ILE—SER—VAL—PRO—TYR—VAL—
GLY—ILE.

12. An improvement according to claim 9 wherein the oligopeptide fragment has the following amino acid sequence:

VAL—VAL—ASN—ASP—HIS—ASN—PRO—THR—LYS—
VAL—THR—SER—LYS—ILE—ARG—VAL—TYR—LEU—
LYS—PRO—LYS.

13. In the production of neutralizing antibodies to poliovirus by immunizing antibody-producing cells with poliovirus antigen in vivo, the improvement of employing isolated poliovirus capsid polypeptide VP1 or oligopeptide fragment thereof as the antigen.

14. An improvement according to claim 13, wherein the oligopeptide fragment has one of the following amino acid sequences:

SER—ILE—PHE—TYR—THR—TYR—GLY—THR—ALA—
PRO—ALA—ARG—ILE—SER—VAL—PRO—TYR—VAL—
GLY—ILE or

VAL—VAL—ASN—ASP—HIS—ASN—PRO—THR—LYS—
VAL—THR—SER—LYS—ILE—ARG—VAL—TYR—LEU—
LYS—PRO—LYS.

* * * * *

UNITED STATES PATENT AND TRADEMARK OFFICE
CERTIFICATE OF CORRECTION

PATENT NO. : 4,751,083
DATED : June 14, 1988
INVENTOR(S) : David Baltimore and Marie B. Chow It is certified that error appears in the above—identified patent and that said Letters Patent is hereby corrected as shown below:

Column 6, line 34 "$pBR_{322}$" should be ---pBR322---.
Column 6, line 43 "$pBR_{322}$" should be ---pBR322---.
Column 7, line 30 "Bacteriaphage" should be ---Bacteriophage---.

Column 12, line 9 "Claim 8" should be ---Claim 3---.

Signed and Sealed this

Seventeenth Day of January, 1989

Attest:

DONALD J. QUIGG

*Attesting Officer*  *Commissioner of Patents and Trademarks*